(12) United States Patent
Howell

(10) Patent No.: US 6,558,354 B1
(45) Date of Patent: May 6, 2003

(54) ADAPTER FOR CONNECTING AN INTRODUCER NEEDLE ASSEMBLY TO A CATHETER INTRODUCER

(75) Inventor: Glade H. Howell, Sandy, UT (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 285 days.

(21) Appl. No.: 09/631,735

(22) Filed: Aug. 4, 2000

(51) Int. Cl.$^7$ ................................................ A61M 5/32
(52) U.S. Cl. ....................................................... 604/162
(58) Field of Search ................................. 604/162, 158, 604/193, 263, 93.01, 523, 48, 9, 164, 110, 168, 104

(56) References Cited

U.S. PATENT DOCUMENTS

| | | | |
|---|---|---|---|
| 4,333,455 A | * 6/1982 | Bodicky | 221/278 |
| 4,613,329 A | * 9/1986 | Bodicky | 356/139.01 |
| 4,747,831 A | 5/1988 | Kulli | 604/110 |
| 4,762,516 A | 8/1988 | Luther et al. | 604/164 |
| 4,894,052 A | * 1/1990 | Crawford | 604/507 |
| 5,000,740 A | 3/1991 | Ducharme et al. | 604/162 |
| 5,409,461 A | 4/1995 | Steinman | 604/110 |
| 5,531,713 A | * 7/1996 | Mastronardi et al. | 604/158 |
| 5,596,988 A | * 1/1997 | Markle et al. | 204/416 |
| 5,601,536 A | 2/1997 | Crawford et al. | 604/263 |
| 5,618,587 A | * 4/1997 | Markle et al. | 118/401 |
| 5,681,291 A | * 10/1997 | Galli | 604/156 |
| 5,695,474 A | * 12/1997 | Daugherty | 604/162 |
| 5,797,880 A | * 8/1998 | Erskine | 604/110 |
| 5,830,190 A | 11/1998 | Howell | 604/168 |
| 5,836,916 A | 11/1998 | Corn | 604/158 |
| 5,992,899 A | * 11/1999 | Strowe | 285/338 |
| 6,004,294 A | 12/1999 | Brimhall et al. | 604/164 |
| 6,027,480 A | 2/2000 | Davis et al. | 604/164 |
| 6,234,999 B1 | * 5/2001 | Wemmert et al. | 604/162 |
| 6,302,906 B1 | * 10/2001 | Goicoechea et al. | 623/1.11 |

FOREIGN PATENT DOCUMENTS

EP     0 827 760 A2     3/1998

* cited by examiner

Primary Examiner—Teresa Walberg
Assistant Examiner—Daniel Robinson
(74) Attorney, Agent, or Firm—James J. Murtha

(57) ABSTRACT

An adapter is provided that allows a single introducer needle assembly having a male luer portion at its distal end to be used with a device having a female luer portion at its proximal end, such as a catheter, and a device without such a female luer portion, such as a catheter introducer.

19 Claims, 3 Drawing Sheets

ADAPTER FOR CONNECTING AN INTRODUCER NEEDLE ASSEMBLY TO A CATHETER INTRODUCER

BACKGROUND OF THE INVENTION

The subject invention relates to an adapter for releasably connecting an introducer needle assembly to a catheter introducer. More specifically, this adapter allows an introducer needle assembly designed for use with a standard intravascular (IV) catheter to be used with a catheter introducer.

Catheters, particularly IV catheters, are used for infusing fluid, such as normal saline solution, various medicaments and total parenteral nutrition, into a patient, withdrawing blood from a patient or monitoring various parameters of the patient's vascular system. Typical peripheral IV catheters tend to be relatively short, and usually are on the order of about two inches or less in length. The most common type of IV catheter is an over the needle peripheral IV catheter. As its name implies, an over the needle catheter is mounted over an introducer needle having a sharp distal tip. The catheter and introducer needle assembly is inserted at a shallow angle through the patient's skin into a blood vessel. Thereafter, the catheter is threaded over the needle and inserted completely into the blood vessel. Once proper placement of the catheter into the blood vessel is confirmed, the clinician withdraws the introducer needle, leaving the catheter in place, and attaches an appropriate device to the catheter. Such a device can include a fluid delivery device, a PRN, a deadender cap or a blood pressure monitoring probe.

In order to attach such devices to a catheter, the catheter includes a hub having a female luer portion at its proximal end. As such, the introducer needle assembly includes a male luer portion at its distal end that extends into and engages the female luer portion of the catheter hub. The male luer portion of the introducer needle assembly thus supports the catheter hub and holds it in the proper orientation to facilitate the insertion of the catheter into a patient.

In contrast to typical peripheral IV catheters, catheter introducers are typically used in conjunction with peripherally inserted central catheters (PICC), or other relatively long, thin and flexible medical devices, to facilitate insertion and placement of the catheter or other medical device into the patient's vasculature. A typical catheter introducer includes a splittable cannula and a hub with a pair of wings fixed to the proximal end of the cannula. An introducer needle assembly is used to place the catheter introducer into the patient. Similar to a typical peripheral IV catheter, the introducer needle is located Within the catheter introducer and both are inserted into a patient in the same general manner as a typical peripheral IV catheter. However, after the clinician withdraws the introducer needle, the clinician inserts the PICC or other relatively long, thin and flexible medical device into the proximal opening of the catheter introducer until the PICC or other medical device is properly placed in the patient's vasculature. After placement of the PICC or other medical device, the clinician grasps the wings and pulls them apart to split the catheter introducer. In this way, the splittable introducer can be removed from the patient over any hub located on the proximal end of the PICC or other medical device.

Since the catheter introducer is not typically connected to another medical device, the hub on the catheter introducer is not configured as a female luer. Instead, the proximal end of the hub has an opening large enough only for the introducer needle to pass therethrough. As such, introducer needle assemblies for use with catheter introducers have a distal portion that is configured to engage the exterior of the hub of the catheter introducer to hold the catheter introducer in the proper orientation on the introducer needle assembly. In addition these introducer needle assemblies must prevent rotation of the catheter introducer with respect to the introducer needle assembly so the wings on the hub are properly aligned with the introducer needle bevel to facilitate proper insertion of the catheter introducer into the patient.

Because of the different configurations of the hub for a typical peripheral IV catheter and a typical catheter introducer, different configurations for the introducer needle assemblies are needed for these different products. The introducer needle assembly used for a typical peripheral IV catheter must have a distal portion that includes a male luer portion that is inserted into and engages the female luer portion of the catheter hub and holds the catheter in an appropriate orientation with the introducer needle. The introducer needle assembly used for a typical catheter introducer must have a distal portion that does not extend into the hub but still holds the catheter introducer in an appropriate orientation with respect to the introducer needle. Specifically, the distal portion of the introducer needle assembly must hold the catheter introducer such that: (a) the distal tip of the catheter introducer is the appropriate distance proximal of the bevel defining the sharp distal tip of the introducer needle; and (b) there is no relative rotation between the catheter introducer and the introducer needle.

However, the need for different introducer needle assemblies for a peripheral IV catheter and a catheter introducer is expensive. Thus, it would be desirable to have an adapter that would allow a single introducer needle assembly having a male luer portion at its distal end to be used with a device having a female luer portion at its proximal end, such as a peripheral IV catheter, and a device without a female luer portion, such as a catheter introducer, and which provides stabilization between the device and the introducer needle assembly and properly axially locates the device with respect to the introducer needle.

SUMMARY OF THE INVENTION

It is therefore an object of this invention to provide an adapter that would allow a single introducer needle assembly having a male luer portion at its distal end to be used with a device having a female luer portion at its proximal end, such as a peripheral IV catheter, and a device without such a female luer portion, such as a catheter introducer and which provides stabilization between the device and the introducer needle assembly and properly axially locates the device with respect to the introducer needle.

The adapter of this invention includes a hollow main body portion with an axial dimension at least about as long as the length of a standard male luer. When the catheter introducer is engaged with the adapter, the distal tip of the catheter introducer is located an appropriate distance proximal of the bevel defining the sharp distal tip of the introducer needle. A flange extends longitudinally from the distal end of the main body portion to engage the proximal end of the catheter introducer. This distally directed flange stabilizes the catheter introducer with respect to the introducer needle. In addition, and if desired, one or more flanges extend longitudinally from the proximal end of the main body portion to engage the distal end of the introducer needle assembly. These proximally directed flanges hold the main body portion of the adapter to the introducer needle assembly. Alternatively, the adapter could dispense with the proximally directed flanges and could be connected to the introducer needle assembly by an adhesive.

The adapter of this invention may be used with any introducer needle assembly typically used with an IV catheter to allow a catheter introducer to be used therewith. For example, it may be used with an introducer needle assembly having spring activated needle retraction mechanism such as shown in U.S. Pat. No. 4,747,831. In addition, the adapter of this invention may be used with other types of shielded introducer needle assemblies, such as shown in U.S. Pat. Nos. 4,762,516; 5,000,740; and 6,004,294, as well as non-shielded introducer needle assemblies.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
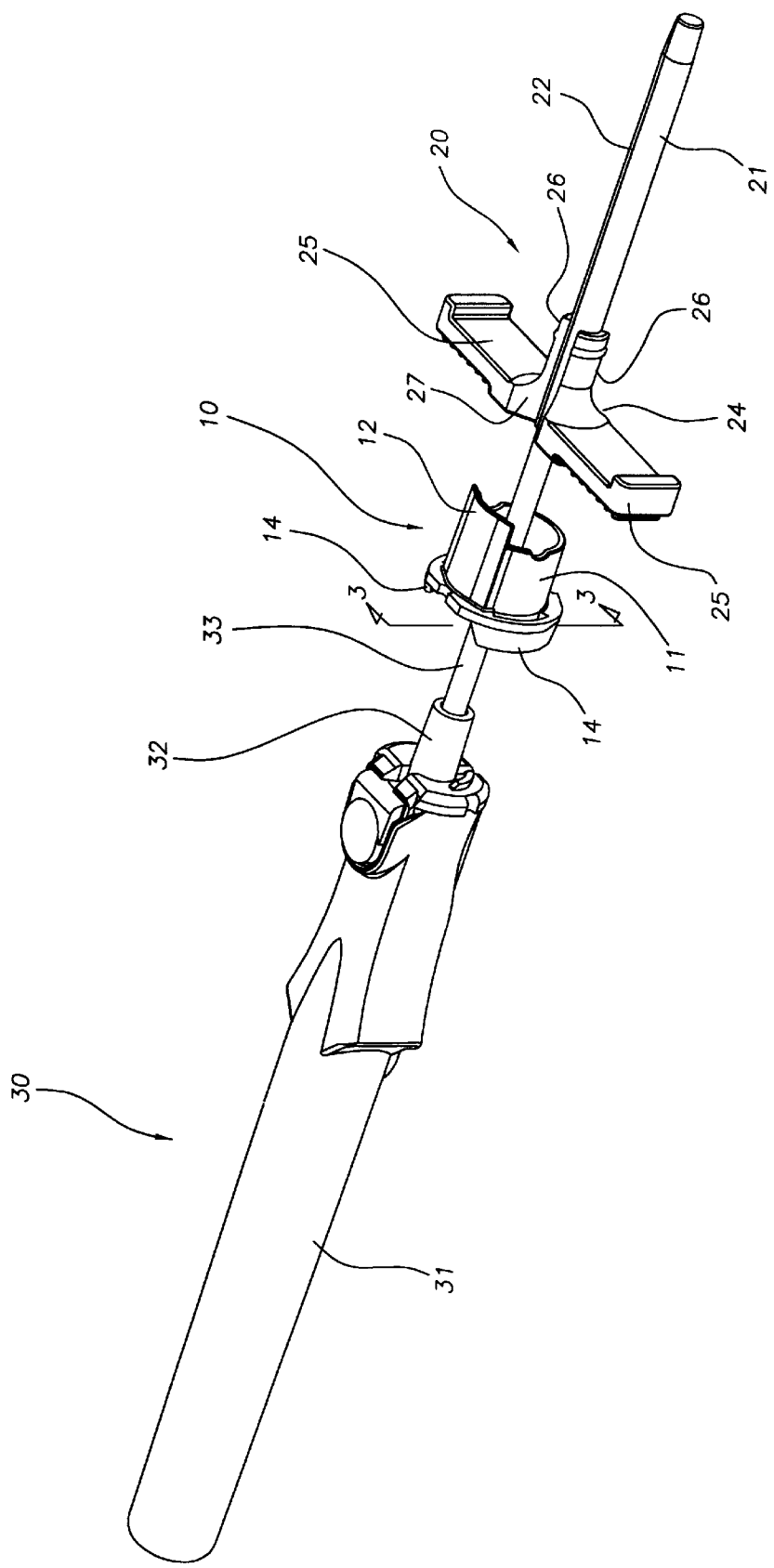
FIG. 1 is an exploded perspective view of an introducer needle assembly having a male luer portion, the adapter of this invention and a catheter introducer without a female luer portion.
Figure 2:
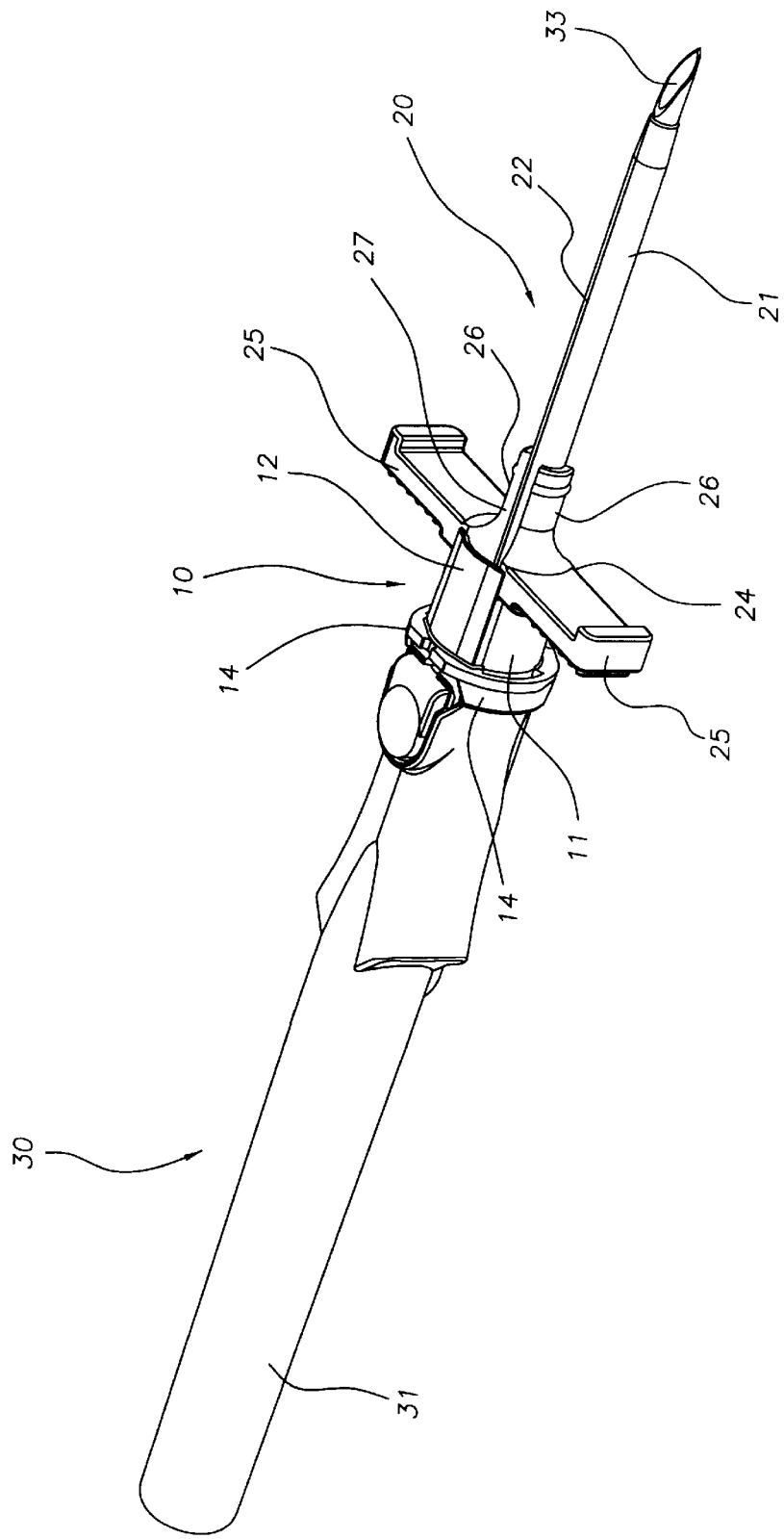
FIG. 2 is a perspective view of the adapter of this invention connected to an introducer needle assembly having a male luer portion and a catheter introducer without a female luer portion.

As used herein, the term "proximal" refers to a location that, during normal use, is closer to the clinician using the device and farther from the patient in connection with whom the device is used. Conversely, the term "distal" refers to a location that, during normal use, is farther from the clinician using the device and closer to the patient in connection with whom the device is used.

As used herein, the term "up" or "upwardly" refers to a location that, during normal use, is radially away from the longitudinal axis of the device and away from the patient's skin. Conversely, as used herein, the term "down" or "downwardly" refers to a location that, during normal use, is radially away from the longitudinal axis of the device and toward the patient's skin.

As used herein, the term "in" or "inwardly" refers to a location that, during normal use, is toward the inside of the device. Conversely, as used herein, the term "out" or "outwardly" refers to a location that, during normal use, is toward the outside of the device.

This invention is described herein using like reference numbers for like elements in the different embodiments. While this invention is satisfied by embodiments in many different forms, there are shown in the drawings and herein described in detail, preferred embodiments of the invention with the scope of the invention measured by the appended claims.

The adapter of this invention is identified generally by the numeral 10. It is used with a catheter introducer 20 and an introducer needle assembly 30. As described herein, introducer needle assembly 30 includes a spring activated needle retraction mechanism such as disclosed in U.S. Pat. No. 4,747,831. However, it is to be understood that it is not required that the adapter of this invention be used with this type of introducer needle assembly. Any other introducer needle assembly having a distal male luer portion may be used with the adapter of this invention.

Catheter introducer 20 includes a splittable cannula 21 and a hub 24 affixed to the proximal end of cannula 21. Such a catheter introducer that may be used with adapter 10 of this invention is disclosed in U.S. Pat. No. 6,027,480.

Suitable materials for cannula 21 include, but are not limited to, thermoplastic resins such as fluorinated ethylene propylene (FEP), polytetrafluoroethylene (PTFE), polyurethane and the like. Cannula 21 includes a pair of longitudinally extending preferential tear lines 22, which are about 165 degrees apart. Preferential tear lines 22 effectively and easily separate cannula 21 into two pieces when cannula 21 is pulled apart. Preferential tear lines 22 can be formed by scoring cannula 21 to provide weakened portions extending longitudinally along cannula 21.

Suitable materials for hub 24 include, but are not limited to, thermoplastic polymeric resins such as polycarbonate, polystyrene, polypropylene and the like. Hub 24 is located at the proximal end of cannula 21 and is formed with a pair of wings 25 radially extending from a pair of shafts 26. Between each wing 25 and shaft 26 is a groove 27. Each wing 25 and associated shaft 26 is aligned on a portion of cannula 21 between each preferential tear line 22 with one of the preferential tear lines 22 located along one groove 27. Thus each groove 27 has a preferential tear line 22 located therein. This arrangement allows the clinician to pull apart wings 25 and split cannula 21 into two portions along preferential tear lines 22.

Introducer needle assembly 30 includes a handle 31 with a male luer portion 32 connected to the distal portion of handle 31. Introducer needle assembly 30 also includes an introducer needle 33. In the embodiment described herein, introducer needle 33 is adapted for proximal movement into handle 31 after introducer needle 33 has been used to insert catheter introducer 20 into a patient. Such a mechanism is described in U.S. Pat. No. 4,747,831.

Adapter 10 includes a main body portion 11 having a distally directed flange 12 extending therefrom. In addition, adapter includes at least one and preferably two proximally directed flanges 14 extending from main body portion Distally directed flange 12 is designed to stabilize and to axially locate catheter introducer 20 with respect to introducer needle assembly 30. If desired, distally directed flange 12 can fit in groove 27 between wings 25. Preferably, distally directed flange 12 engages wings 25 with an interference fit although, if desired, flange 12 and wings 25 could each include cooperating detent mechanisms to provide for mechanical engagement between the two. In either event, flange 12 holds catheter introducer 20 and prevents unwanted rotation of catheter introducer 20. Although in the preferred embodiment only one distally directed flange 12 is used, it is within the scope of this invention to have a plurality of distally directed flanges engaging wings 25.

Proximally directed flanges 14 are designed to engage the distal portion of handle 31. Flanges 14 can engage the distal portion of handle 31 with an interference fit. If desired, flanges 14 and the distal portion of handle 31 can include cooperating detent mechanisms so that flanges 14 mechanically engage handle 31. Alternatively, main body portion 11 can be fitted to handle 31 by adhesion or some other mechanism that does not require the use of proximally directed flanges 14.

Figure 3:
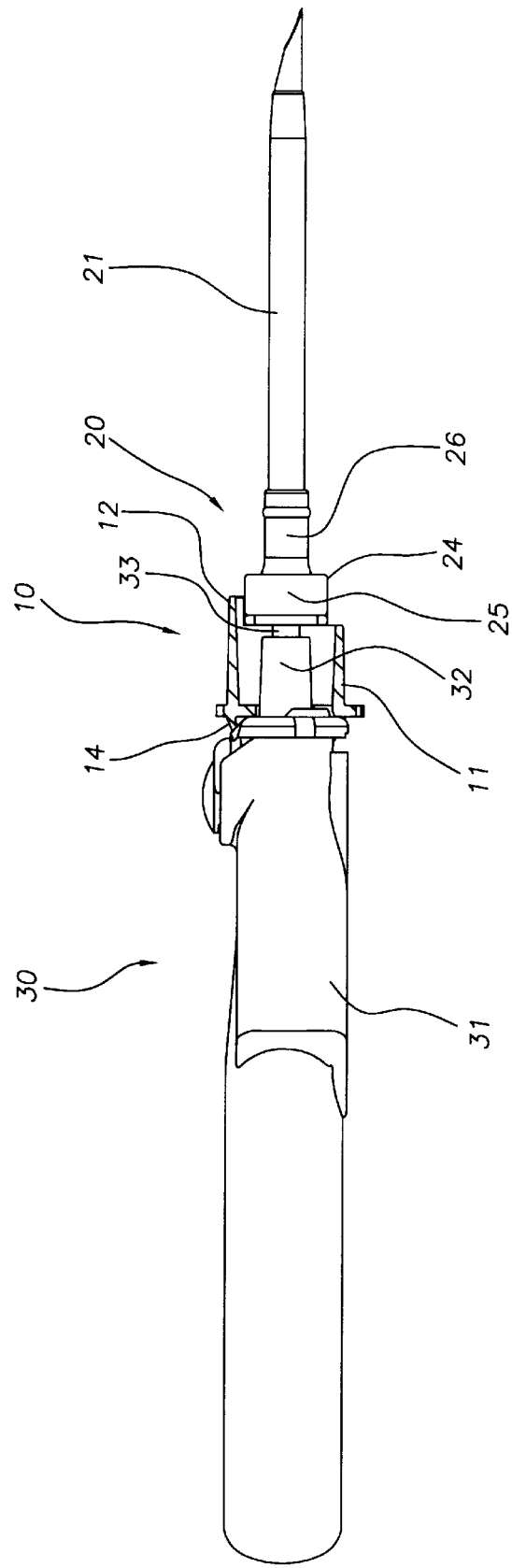
FIG. 3 is a cross-sectional view of the adapter of this invention, taken along line 3—3 of FIG. 1, connected to an introducer needle assembly having a male luer portion and a catheter introducer without a female luer portion.

Main body portion 11 should be long enough so that when flanges 14 engage handle 31, the distal end of main body portion is at least aligned with the distal end of male luer portion 32. Thus, main body portion 11 should be at least as long as the length of male luer portion 32. Typically, a standard male luer portion of a medical device is on the order of about 7.5 millimeters long. Preferably, the distal end of main body portion is slightly distal of the distal end of male luer portion 32. See FIG. 3.

In this way, introducer needle assembly 30, which is designed for use with a catheter having a female luer portion at its proximal end can be adapted for use with catheter introducer 20 that has no such female luer portion. In addition, adapter 10 may facilitate the visualization of blood flashback toward the distal end of introducer needle assembly 30. See, e.g. U.S. Pat. No. 5,830,190.

Thus, it is seen that an adapter is provided that allows a single introducer needle assembly having a male luer portion at its distal end to be used with a device having a female luer portion at its proximal end, such as a peripheral IV catheter, and a device without such a female luer portion, such as a catheter introducer and which provides stabilization between the device and the introducer needle assembly and properly axially locates the device with respect to the introducer needle.

I claim:

1. An adapter to hold a catheter introducer to an introducer needle assembly, the introducer needle assembly having a distal male luer portion, the adapter comprising: a main body portion having a distally directed flange for engagement with the introducer catheter.

2. The adapter of claim 1 further comprising at least one proximally directed flange for engagement with the introducer needle assembly.

3. The adapter of claim 2 further comprising two proximally directed flanges for engagement with the introducer needle assembly.

4. The adapter of claim 1 wherein the main body portion has a length at least as long as the distal male luer portion of the introducer needle assembly.

5. The adapter of claim 4 wherein the main body portion has a length of at least about 7.5 millimeters.

6. The adapter of claim 4 further comprising at least one proximally directed flange for engagement with the introducer needle assembly.

7. The adapter of claim 6 further comprising two proximally directed flanges for engagement with the introducer needle assembly.

8. An adapter to selectively maintain a catheter introducer in position with respect to an introducer needle assembly, wherein the catheter introducer includes a cannula attached to a hub, and the hub includes an engaging surface, and wherein the introducer needle assembly includes a handle, a male luer portion attached to a distal end of the handle, and a needle attached to the male luer portion, the adapter comprising:

a main body portion sized to receive the male luer portion of the introducer needle assembly; and a distally-directed flange adapted to engage the engaging surface of the hub.

9. The adapter of claim 8 further comprising a proximally-directed flange mounted to the main body portion and adapted to engage the introducer needle assembly in an interference fit.

10. The adapter of claim 8 wherein the hub includes wings and wherein the engaging surface is a groove disposed between the wings, wherein the distally directed flange is sized to fit within the groove in an interference fit to prevent relative rotation of the adapter and the catheter introducer.

11. The adapter of claim 10 further comprising a proximally-directed flange adapted to engage the introducer needle assembly to prevent relative rotation of the adapter and the introducer needle assembly.

12. The adapter of claim 11 wherein the proximally-directed flange is adapted to engage the handle of the introducer needle assembly.

13. The adapter of claim 8 wherein the main body portion has a cylindrical shape, further comprising a proximally-directed flange mounted to the main body portion and adapted to engage the handle of the introducer needle assembly to prevent relative rotation of the adapter and the introducer needle assembly, and wherein the hub includes wings and the engaging surface is a groove, wherein the distally directed flange is sized to fit within the groove to prevent relative rotation of the adapter and the catheter introducer.

14. A catheter introducer insertion device comprising:

a catheter introducer including a splittable cannula attached to a hub, wherein the hub includes an engaging surface;

an introducer needle assembly including a handle, a male luer portion attached to a distal end of the handle, and a needle attached to the male luer portion; and an adapter including a main body portion sized to receive the male luer portion of the introducer needle assembly and a distally-directed flange adapted to engage the engaging surface of the hub in an interference fit.

15. The catheter introducer insertion device of claim 14 further comprising a proximally-directed flange mounted to the main body portion and adapted to engage the introducer needle assembly.

16. The catheter introducer insertion device of claim 14 wherein the hub includes wings and wherein the engaging surface is a groove, wherein the distally directed flange is sized to fit within the groove to prevent relative rotation of the adapter and the catheter introducer.

17. The catheter introducer insertion device of claim 16 further comprising a proximally-directed flange adapted to engage the introducer needle assembly to prevent relative rotation of the adapter and the introducer needle assembly.

18. The catheter introducer insertion device of claim 17 wherein the directed flange is adapted to engage the handle of the introducer needle assembly.

19. The catheter introducer insertion device of claim 14 wherein the main on has a cylindrical shape, further comprising a proximally-directed flange the main body portion and adapted to engage the handle of the introducer assembly to prevent relative rotation of the adapter and the introducer needle and wherein the hub includes wings and the engaging surface is a groove, e distally directed flange is sized to fit within the groove to prevent relative the adapter and the catheter introducer.

* * * * *